United States Patent [19]

Hafner et al.

[11] Patent Number: 4,968,668

[45] Date of Patent: Nov. 6, 1990

[54] ALCOHOLS HAVING 3-METHYL OR 3,5-DIMETHYL OR 3,5-DIMETHYLPHENYL GROUPS, A PROCESS FOR THEIR PREPARATION AND A FRAGRANCE COMPOSITION CONTAINING SAME

[75] Inventors: Walter Hafner, Eurasburg; Walter Gebauer, Munich; Marlies Regiert, Munich; Wilhelm Friedrich, Munich; Erich Markl, Munich, all of Fed. Rep. of Germany

[73] Assignee: Consortium fur Elektrochemische Industrie GmbH, Munich, Fed. Rep. of Germany

[21] Appl. No.: 382,646

[22] PCT Filed: Feb. 4, 1988

[86] PCT No.: PCT/EP88/00081

§ 371 Date: Aug. 7, 1989

§ 102(e) Date: Aug. 7, 1989

[87] PCT Pub. No.: WO88/05770

PCT Pub. Date: Aug. 11, 1988

[30] Foreign Application Priority Data

Feb. 6, 1987 [DE] Fed. Rep. of Germany ....... 3703584

[51] Int. Cl.$^5$ .................. A61K 4/46; C07C 33/18
[52] U.S. Cl. .................................. 512/20; 512/25; 568/715; 568/814
[58] Field of Search .............. 512/20, 25; 568/814, 568/715

[56] References Cited

U.S. PATENT DOCUMENTS

| 4,490,284 | 12/1984 | Brunke et al. ............ 512/20 |
| 4,549,983 | 10/1985 | Wiegers et al. ........... 512/20 |
| 4,710,316 | 12/1987 | Hafner et al. ............ 512/20 |

FOREIGN PATENT DOCUMENTS

| 0045534 | 2/1982 | European Pat. Off. ...... 512/21 |
| 0287084 | 10/1988 | European Pat. Off. ..... 512/20 |
| 0035064 | 3/1980 | Japan ................... 512/20 |
| 0076431 | 4/1986 | Japan ................... 512/20 |

*Primary Examiner*—Werren B. Lone
*Attorney, Agent, or Firm*—Collard, Roe & Galgano

[57] ABSTRACT

2-Methyl-3-(3-methylphenyl)-propan-1-ol, 2-methyl-3-(3,5-dimethylphenyl)-propan-1-ol, 1-(3-methylphenyl)-2-methylbutan-3-ol and 1-(3,5-dimethylphenyl)-2-methylbutan-3-ol, their preparation and use as fragrances.

2 Claims, No Drawings

ALCOHOLS HAVING 3-METHYL OR 3,5-DIMETHYL OR 3,5-DIMETHYLPHENYL GROUPS, A PROCESS FOR THEIR PREPARATION AND A FRAGRANCE COMPOSITION CONTAINING SAME

3-Phenylpropionaldehyde and 3-phenylpropan-1-ol have long been used as fragrances. Furthermore, the fragrant character of propionaldehydes of the general formula

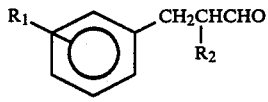

is disclosed in Japanese Published Specification JP 61,194,045 (CA 106:32752m).

The use of 1,1-di($C_1$-$C_6$-alkyl)-2-phenylethane derivatives as perfumes is disclosed in European patent application No. 0 076,493. However, all compounds described therein exhibit no additional substitution of the phenyl radical, such as is evident, for example, for 2,2-dimethyl-3-phenylpropanol in Example 2 of this specification.

It has now been found that new fragrances having a predominantly floral character are formed by methyl substitution in the 3- or 3,5-position of the benzyl radical.

The invention relates to 2-methyl-3-(3-methylphenyl)-propan-1-ol, 2-methyl-3-(3,5-dimethylphenyl)-propan-1-ol, 1-(3-methylphenyl)-2-methylbutan-3-ol and 1-3,5-dimethylphenyl)-2-methylbutan-3-ol.

A process for the preparation of 2-methyl-3-(3-methylphenyl)-propan-1-ol and 2-methyl-3-(3,5-dimethylphenyl)-propan-1-ol comprises (a) reacting 3-methylbenzaldehyde or 3,5-dimethylbenzaldehyde with propionaldehyde in the presence of bases and
(b1) hydrogenating the reaction product from (a), or
(a1) reacting 3-methylbenzylmagnesium chloride or 3,5-dimethylbenzylmagnesium chloride with chloroacetone and
(b) catalytically hydrogenating the reaction product from (a1) after base-catalyzed cyclization.

These reaction pathways are illustrated by the following reaction schemes.

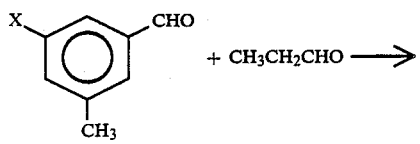

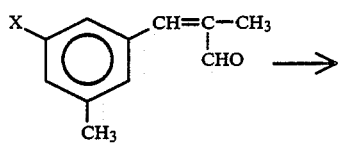

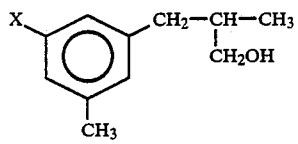

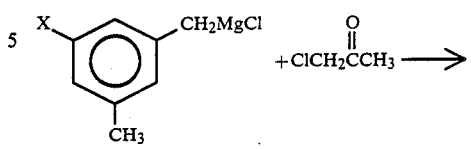

X = H, $CH_3$.

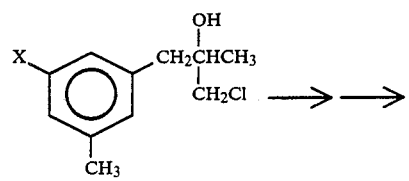

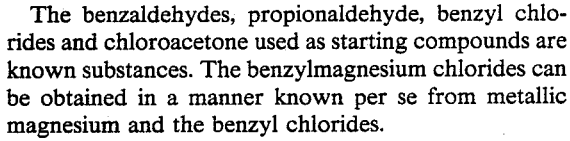

The benzaldehydes, propionaldehyde, benzyl chlorides and chloroacetone used as starting compounds are known substances. The benzylmagnesium chlorides can be obtained in a manner known per se from metallic magnesium and the benzyl chlorides.

The reaction in accordance with (a) is preferably carried out using alkali metal hydroxides, in particular sodium hydroxide or potassium hydroxide, at temperatures of preferably −5° C. to 80° C. in polar solvents such as alcohols, for example methanol or ethanol. The reaction product in accordance with (a) is then hydrogenated using reduction catalysts such as palladium on active carbon or Raney nickel and hydrogen and the alcohol is finally separated by fractional distillation.

The reaction in accordance with (a1) is preferably carried out at temperatures from 0° C. to 60° C. in dry inert solvents such as diethyl ether and/or tetrahydrofuran with subsequent hydrolysis ideally in the presence of mineral acids such as hydrochloric acid, sulfuric acid and the like. The reaction product according to (a1) is subsequently cyclized to the epoxide using bases, preferably alkali metal hydroxides such as sodium hydroxide or potassium hydroxide, at temperatures of preferably from 0° C. to 50° C., then catalytically hydrogenated, preferably using reduction catalysts such as palladium on active carbon and hydrogen and the alcohol is finally separated by fractional distillation.

A further process for the preparation of 2-methyl-3-(3-methylphenyl)-propan-1-ol and 2-methyl-3-(3,5-dimethylphenyl)-propan-1-ol comprises (a2) reacting 3-methylbenzyl chloride or 3,5-dimethylbenzyl chloride with diethyl methylmalonate,
(b2) thermally decarboxylating the reaction product from (a2) after hydrolysis and
(c2) hydrogenating the reaction product from (b2) or
(a3) reacting 3-methylbenzaldehyde or 3,5-dimethylbenzaldehyde with methyl 2-bromopropionate and, after elimination of water,
(b3) hydrogenating the reaction product from (a3).

These reaction pathways are illustrated by the following reaction schemes.

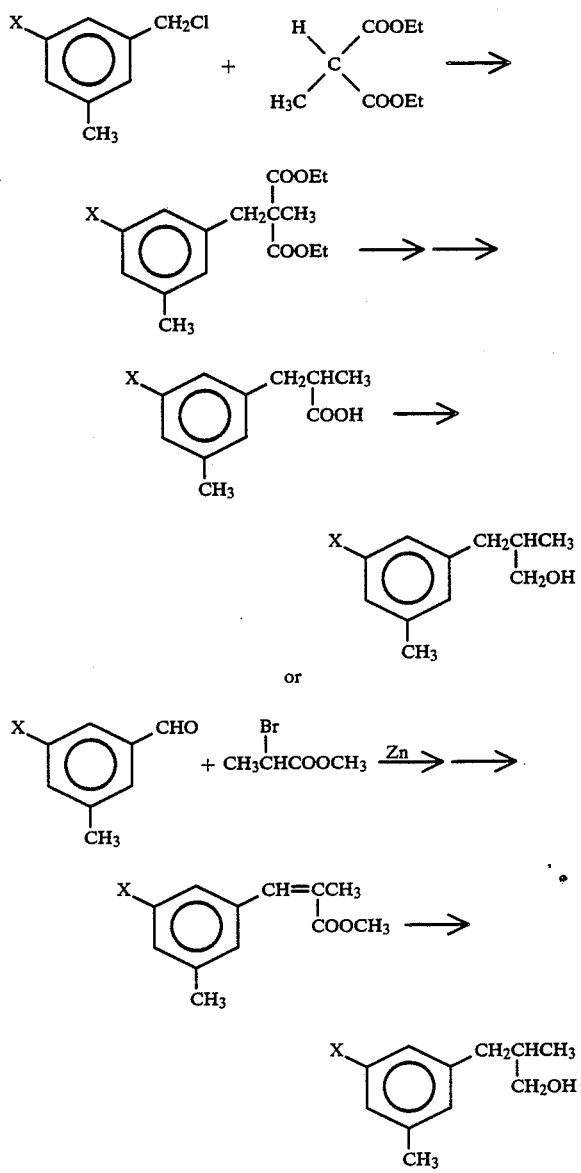

Diethyl methylmalonate and methyl 2-bromopropionate are known compounds. The reaction in accordance with (a2) is preferably carried out at temperatures from 70° to 120° C. in the presence of a base such as sodium carbonate or potassium carbonate. After hydrolysis, for example using bases such as sodium hydroxide or potassium hydroxide, the product is thermally decarboxylated, preferably at 120° C. to 150° C. The acid obtained or the esterification product with alcohols such as methanol or ethanol is reacted with hydrogenating agents such as lithium aluminum hydride or hydrogen in the presence of a suitable catalyst.

The reaction in accordance with (a3) is preferably carried out at temperatures from 80° C. to 110° C. in the presence of metallic zinc. After elimination of water, the ester obtained is reacted with hydrogenating agents such as lithium aluminum hydride or hydrogen in the presence of a suitable catalyst.

Processes for the preparation of 1-(3-methylphenyl)-2-methylbutan-3ol and 1-(3,5-dimethylphenyl)-2-methylbutan-3-ol comprise reacting 2-methyl-3-(3-methylphenyl)-propanol or 2-methyl-3-(3,5-dimethylphenyl)propanol with methylmagnesium halide (halogen=Cl, Br, I)

or reacting 3-methylbenzyl chloride or 3,5-dimethylbenzyl chloride with methyl ethyl ketone in an organic/alkaline 2-phase system in the presence of a phase transfer catalyst.

Methyl halides and methyl ethyl ketone are known. The methylmagnesium halides can be obtained in a manner known per se from metallic magnesium and the methyl halides. The reaction of the propanals with the methylmagnesium halide is preferably carried out at temperatures from 0° to 50° C. in dry inert solvents such as diethyl ether and/or tetrahydrofuran with subsequent hydrolysis ideally in the presence of mineral acids such as hydrochloric acid, sulfuric acid and the like.

In the reaction of benzyl chloride with methyl ethyl ketone, the reactants are employed in approximately equimolar amounts, or methyl ethyl ketone is employed in excess. The organic/alkaline 2-phase system is formed from an organic water-immiscible inert solvent and a 5-50% strength by weight aqueous solution of alkali metal hydroxide or alkali metal hydroxide present in solid form. Examples of alkali metal hydroxides are sodium hydroxide or potassium hydroxide. Phase transfer catalysts which are employed are, for example, crown ethers or quaternary ammonium or phosphonium salts in amounts of 0.5-5 mol-% based on benzyl chloride.

Regarding further details, reference should be made expressly to the examples.

The compounds according to the invention are used as fragrances.

The alcohols according to the invention have a very wide area of application on account of their stability to air and liquors. In addition to use in perfumery, they are suitable for perfuming detergents and cleaners, textiles, plastic products and the like.

EXAMPLE 1

2-Methyl-3-(3-methylphenyl)-propan-1-ol 7.5 g of KOH were dissolved in 240 ml of ethanol in all four-necked flask with stirring and flushing with argon. First 123 g of 3-methylbenzaldehyde, then, in the course of about 4 hours, 62 g of propionaldehyde were added with ice cooling. The reaction temperature was 8° C. Subsequently, small pieces of ice, softened water and ether were added to the mixture. The lower layer was discarded, and the upper layer was washed with 300-400 ml of water and then distilled through a 20-cm long column containing 7 mm glass helices. 116 g of 2-(3-methylbenzylidene)-propionaldehyde were obtained at 80°-90° C. and 0.2 mbar. 35 g of this compound, 100 ml of cyclohexane and 1 g of hydrogenation catalyst (5% Pd on active carbon) were put into a 0.5 l shaking autoclave. The autoclave was pressurized to 70 bar with hydrogen at 25° C. and shaken at 40° C. for 7 hours. Distillation through a rotating band column gave 15 g of 2-methyl-3-(3-methylphenyl)-propan-1-ol (boiling point 70° C. at 0.1 mbar).

EXAMPLE 2

2-Methyl-3-(3,5-dimethylphenyl)-propan-1-ol 25 g of magnesium turnings and 155 g of 3,5-dimethylbenzyl chloride were reacted in 300 ml of ether. After dilution with 200 ml of tetrahydrofuran, a mixture of 92.5 g of chloroacetone and 100 ml of tetrahydrofuran was added dropwise with ice cooling in the course of one hour. After reacting for 2 hours at 25° C., the mixture was poured onto a mixture of ice and 2.5 mol hydrochloric acid. The upper layer was separated off and the aqueous layer was extracted with ether. The combined organic layers were washed with water until neutral, dried using $Na_2SO_4$, filtered and distilled. 110 g of 1-chloro-2-(3,5-dimethylbenzyl)-propan-2-ol were obtained at 110°–112° C./0.2 mbar. 109 g of this compound were stirred at 30° C. for 2 hours with 20 ml of methyl tert.-butyl ether and a solution of 31 g of NaOH in 750 ml of water. The layers were then separated, and the organic phase was washed with water until neutral, dried using $Na_2SO_4$ and distilled. 65 g of 2-(3,5-dimethylbenzyl)-propylene oxide were obtained at a boiling point of 68°–70° C./0.3 mbar. 80 g of this compound were dissolved in 100 ml of cyclohexane and put into a 0.5 l shaking autoclave with 0.8 g of 5% Pd on active carbon. After flushing with inert gas, the autoclave was pressuried with hydrogen (130 bar) and heated at 150° C. for 8 hours. The cooled mixture was depressurized, flushed with inert gas, the catalyst was filtered off and the filtrate was distilled through a 30-cm long column containing steel helices. 18 g of 2-methyl-3-(3,5-dimethylphenyl)-propan-1-ol passed over at 80°–81° C./0.07 mbar.

EXAMPLE 3

Methyl-3-(3-methylphenyl)-propan-1-ol 500 ml of toluene, 207 g of ground potassium carbonate, 8 g of potassium iodide, 7 g of 18-crown-6 and 209 g of diethyl methylmalonate were initially introduced into a 2 l four-necked flask. The mixture was heated to 85° C. with stirring. 141 g of 3-methylbenzyl chloride were added dropwise in the course of half an hour and the mixture was then stirred at 90° C. for 8 hours. After cooling, the salts were removed by repeatedly shaking with water and the organic layer was distilled. 184 g of diethyl 2-methyl-2-(3-methylbenzyl)-malonate were obtained at a boiling point of 120° C. and a pressure of about 0.02 mbar. For hydrolysis, the ester was boiled under reflux with stirring for 16 hours with 60 g of NaOH, 170 ml of water and a spatula tip-full of tetradecyltrimethylammonium bromide, ethanol which formed in the meantime being distilled off. The dicarboxylic acid was liberated by acidifying with hydrochloric acid, separated off and heated in xylene for 4 hours under reflux for decarboxylation. The monocarboxylic acid was then esterified with ethanol (p-toluenesulfonic acid as catalyst, cyclohexane as entraining agent for water). 115 g of ethyl 2-(3-methylbenzyl)-propionate (boiling point 70°–73° C. at 0.03 mbar) were obtained. For hydrogenation, 21 g of $LiAlH_4$ were dissolved or suspended in 800 ml of tetrahydrofuran in a 2 l four-necked flask under nitrogen. A mixture of 110 g of ethyl 2-(3-methylbenzyl)-propionate and 100 ml of tetrahydrofuran were then added dropwise with ice cooling. The mixture was then decomposed with ice and hydrochloric acid, extracted with ether and dried over $K_2CO_3$, and 75 g of 2-methyl-3-(3-methylphenyl)-propan-1-ol (boiling point 68°–70° C. at 0.1 mbar) were obtained by distillation.

Odor Pattern: watery-floral, green-fruity

EXAMPLE 4

2-Methyl-3-(3,5-dimethylphenyl)-propan-1-ol

Example 3 was repeated with 3,5-dimethylbenzyl chloride. 2-Methyl-3-(3,5-dimethylphenyl)-propan-1-ol (boiling pint 83° C. at 0.1 bar) was obtained.

Odor note: rosy, green

EXAMPLE 5

1-(3-Methylphenyl)-2-methylbutan-3-ol 256 g of methyl ethyl ketone, 80 g of powdered NaOH, 28 g of calcium oxide and 10 g of tetrabutylammonium bromide were warmed with stirring. 141 g of 3-methylbenzyl chloride were added dropwise in the course of 90 minutes at 70° C. The mixture was then boiled under reflux for 1 hour, cooled, filtered and washed with methyl ethyl ketone, and the filtrate was concentrated and distilled through a 30-cm long column containing steel helices. 86% pure 3-(3-methylbenzyl)-butanone was obtained at a boiling point of 80° C. at 0.4 mbar in 40% yield.

A solution of 1 mol of 3-(3-methylbenzyl)-butanone (86% pure) in 300 ml of isopropanol was added dropwise in the course of 5 hours to 100 g of aluminum triisopropylate heated to boiling with 300 ml of isopropanol, while a mixture of acetone and isopropanol distilled off slowly through a 50-cm long packed column. After reacting for 8 hours, the distillate no longer contained any acetone. The residual isopropanol was then distilled off and 300 ml of toluene, 300 g of ice and 300 g of conc. hydrochloric acid were added to the residue. The layers were separated, the aqueous phase was extracted with 300 ml of toluene, and the combined organic phases were extracted by shaking with a little water, concentrated and distilled through a Vigreux column at 0.2 mbar. A mixture of 1-(3-methylphenyl)-2-methylbutan3-ol isomers was obtained in 85% yield from 78°–80° C.

Odor pattern: green-rosy, somewhat ambered with lime blossom and lilies of the valley.

What is claimed is:
1. A compound selected from the group consisting of 2-methyl-3-(3,5-dimethylphenyl)-propan-1-ol, 1-(3-methyl-phenyl)-2-methylbutan-3-ol and 1-(3,5-dimethylphenyl)-2-methylbutan-3-ol.
2. A fragrance composition, comprising:
a compound selected from the group consisting of 2-methyl-3-(3-(3-methylphenyl)-propan-1-ol, 2-methyl-3-(3,5-dimethylphenyl)-propan-1-ol, 1-(3-methyl-phenyl)-2-methylbutan-3-ol, 1-(3,5-dimethylphenyl)-2-methylbutan-3-ol and a combination thereof; and,
a carrier substance.

* * * * *